United States Patent [19]

Eriksson et al.

[11] 4,078,863

[45] Mar. 14, 1978

[54] MEASURING THE CONCENTRATION OF SUBSTANCES SUSPENDED IN A LIQUID

[75] Inventors: Lennart Eriksson, Vallentuna; Gerdt Fladda; Jan Hill, both of Taby, all of Sweden

[73] Assignee: Svenska Traforskningsinstitutet, Stockholm, Sweden

[21] Appl. No.: 606,132

[22] Filed: Aug. 19, 1975

[30] Foreign Application Priority Data

Aug. 28, 1974 Sweden .............................. 7410882

[51] Int. Cl.$^2$ .......................................... G01N 21/00
[52] U.S. Cl. ..................................... 356/104; 356/102
[58] Field of Search ................. 356/39, 102, 103, 104, 356/208

[56] References Cited

U.S. PATENT DOCUMENTS

| 3,275,834 | 9/1966 | Stevens ................................ 356/102 |
| 3,662,176 | 5/1972 | Kamentsky et al. ................356/39 X |
| 3,740,148 | 6/1973 | Moroz et al. .......................... 356/102 |
| 3,785,735 | 1/1974 | Friedman et al. ...................... 356/39 |
| 3,786,261 | 1/1974 | Tucker ............................ 356/208 X |

*Primary Examiner*—John K. Corbin
*Assistant Examiner*—Matthew W. Koren
*Attorney, Agent, or Firm*—Pollock, Vande Sande & Priddy

[57] ABSTRACT

This invention relates to improvements in measuring the concentration of suspended substances in a liquid, the substances consisting of components of different geometrical size. The liquid is flowing in a pipe and is illuminated transverse to its flow direction by one or more light sources. A detecting means is arranged to detect light spread by the suspended substances in the liquid in another direction than that of the illuminating incident radiation. This detecting means delivers two electrical signals, the first of which represents a D.C. level measured during a predetermined time and corresponding to a detected level of luminous intensity. The second signal represents the number of times during the same said predetermined time that the detected level of luminous intensity has exceeded a definite discriminator level. The equation of the first signal is $Ug = cPF + dFF$ and the equation of the second signal is $UF = aPF + bFF$, where $a$, $b$, $c$ and $d$ are constants, $b$ is substantially less than $a$, $c$ and $d$; and PF represents the concentration of suspended material in excess of a certain definite geometrical size; and FF the concentration of suspended material below the same size. The signals from the detecting means are fed to an evaluation means to develop an output signal, which is representative of the sum $S = PF + FF$ of the total concentration of substances of the flowing liquid during the predetermined time. As an alternative, the evaluation means also develops output signals, representative of the concentration of PF and FF separately.

7 Claims, 2 Drawing Figures

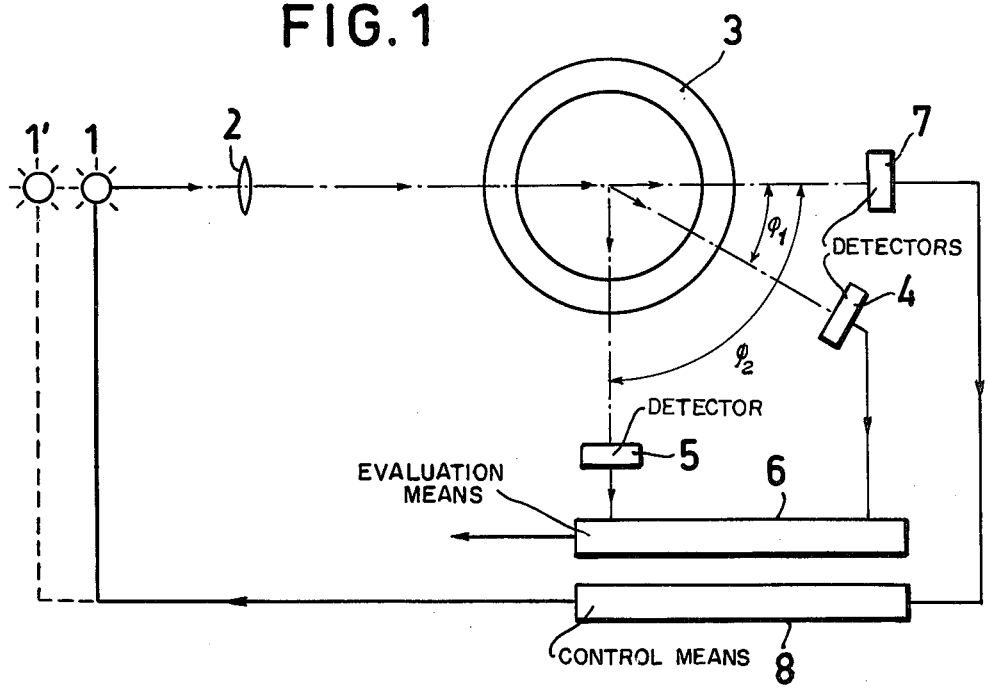
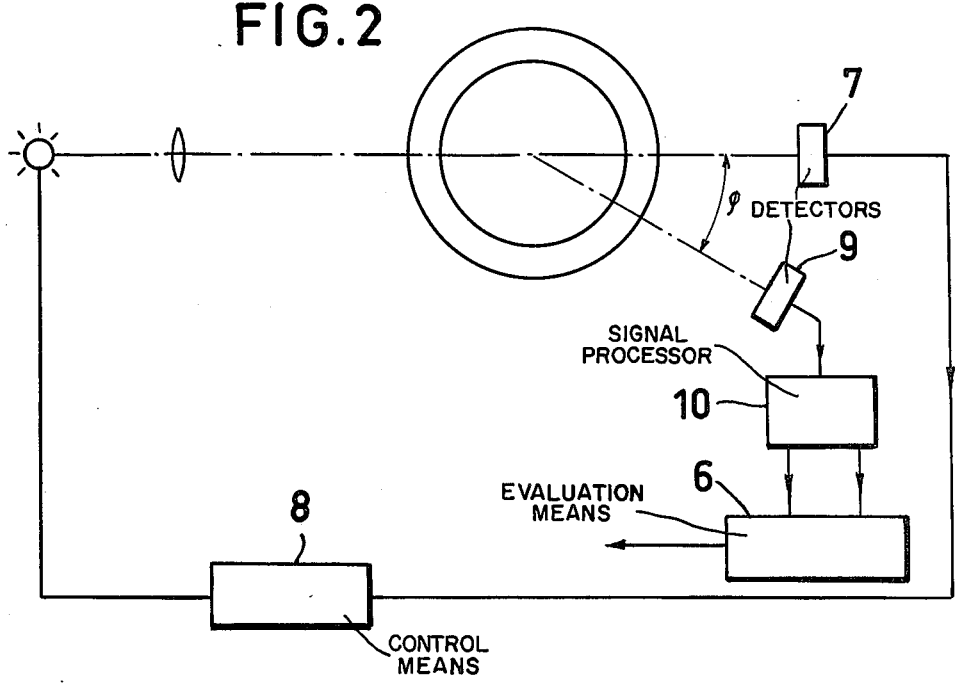

MEASURING THE CONCENTRATION OF SUBSTANCES SUSPENDED IN A LIQUID

BACKGROUND OF THE INVENTION

This invention relates to improvements in measuring the concentration of suspended substances in a liquid, the substances consisting of components of different geometrical size. The liquid is arranged to flow and is illuminated transverse to its flow direction by one or more light sources. The radiation emitted from the liquid is detected.

Especially in the wood-processing industry it is of the greatest interest to be able to measure the concentration of suspended substances, mainly fibers and fiber fragments, in waste water of different types. According to standard methods now in use suspended substances means such materials as can be removed mechanically by means of filtration. These suspended substances may consist of many different components, mainly fiber materials, as well as different fillers from paper manufacture, which may vary considerably in size.

The instruments now available for measuring suspended substances, such as turbidimeters, are based on the general light scattering ability of the sample. Measuring means operating with polarized light permit determination of the concentration of suspended substances provided variations of composition do not occur. However, the existence of such variations is typical of waste water systems in the wood-processing industry, particularly during so-called occasional discharges, as a consequence of disturbance or functional trouble in the manufacturing process.

Instruments for measuring turbidity are often considerably more sensitive to discharges of a fine fraction (fiber fragments) than to discharges of first-rate fibers, and therefore an increase of the output signal from an instrument of this type may mean a big discharge of first-rate fibers or else a considerably less discharge of a fine fraction.

As fibers have a great value it is of interest to recycle fibers in waste water to production. If these fibers leave the external purification plants of the manufacturer, they may collect in fiber banks near to the discharge. On the other hand, the fine fraction may be suspended in the water for a long time and may cause an environmental disturbance of another kind. An increased number of first-rate fibers in a drain is often an indication that something in the system has gone wrong and must be corrected. Therefore it is often of interest to measure selectively the amount of first-rate fibers in a discharge. There is an instrument on the market, which substantially only reacts to the amount of first-rate fibers in a discharge, but is not sensitive in any degree worth mentioning to the amount of fine fraction. One conclusion is that there is no instrument today that can measure continuously the concentration of suspended substances in the connection with wood-processing industry in a sufficiently reliable way, if no special conditions are present.

The guiding principles of today for control of activity dangerous to the environment in the forest industry indicate that the concentration of suspended substances delivered by a manufacturer to a recipient stream or other body of water should be measured and reported to the authorities. The sharpened demands on control have also stressed the need of continuously recording instruments that can discover rapid fluctuations of the concentration level.

So far measurements of suspended substances in the forest industry have been carried out in the laboratories of the manufacturers by means of mechanical separation of a sample. The sample usually is obtained by means of an automatic sampler collecting samples at regular intervals for comparison to a standard sample, usually daily. This method is slow and relatively expensive, as it requires manual handling, and it will provide different results for different compositions of the sample. The advantage of the method is that it functions and is simple. The exactness is satisfactory, but care must be taken to maintain it. However, the method is only suitable for control of random samples.

OBJECT OF THE INVENTION

An object of the invention is to provide an instrument by means of which the total concentration of suspended substances is obtained with a great exactness as the sum of the concentration of first-rate fibers and the concentration of fine fraction. Consequently, the invention combines the advantages of the different types of the instruments described above and evades the weaknesses of those instruments for measuring the total concentration of suspended substances.

SUMMARY OF THE INVENTION

A first detecting means is arranged to detect light scattered by the suspended substances in the liquid in another direction than that of the illuminating incident radiation. The detecting means delivers two electrical signals, the first of which represents a D.C. level measured during a predetermined time and corresponding to a detected level of lumious intensity; and the second of which represents a number of times based on the same said predetermined time that the detected level of luminous intensity has exceeded a definite discriminator level. The equation of the first signal is $Ug = cPF + dFF$ and the equation of the second signal is $UF = aPF + bFF$, where $a$, $b$, $c$ and $d$ are constants; $b$ is substantially less than $a$, $c$ and $d$; PF represents the concentration of suspended material in excess of a certain definite geometrical size; and FF, the concentration of suspended material below the same size. The signals from the detecting means are fed to an evaluation means to develop an output signal, which is representative of the sum $S = PF + FF$, of the total concentration of substances of the flowing liquid, said substances being suspended during the predetermined time. As an alternative, the evaluation means also develops output signals, which are representative of the concentrations of PF and FF separately. Besides indicating the total concentration of suspended substances the device can also indicate the amounts of first-rate fibers and the amount of fine fraction. The method of the invention provides a possibility of a more continuous control of how different components vary in time, by means of which changes will be early discovered.

The method of the invention is based on the fact that if a flowing liquid with suspended material is illuminated, the light incident to the liquid will be scattered by its reflection from the particles present in the liquid. The intensity of light scattered in a definite direction becomes greater, in accordance with observations made, as the size of the particle increases from which the light has been scattered. When a fiber-containing liquid is illuminated and the light scattered in one direction is caught by a detector and converted into an electrical signal, a strongly varying signal is obtained, which can be primarily characterized as a D.C. current with a superimposed noise signal of different high amplitudes and frequency. The signal has been obtained by the scattering of the light from fibers of different size, which fibers have each contributed to the resulting signal.

On a closer analysis of the signal it can be established that as scattering from bigger fibers will provide a great contribution to the signal in the form of a pulse spike it is possible to obtain the concentration of fibers in excess of a definite size by calculating the number of times at which the signal exceeds a definite threshold level, i.e., the number $U_f = aPF$, where $a$ is a constant and PF is the concentration of fibers in excess of a definite size ("first-rate fibers"). The constant $a$ is primarily dependent on the selected time, the selected level and the relative type of fiber material. Certainly scattering from separate smaller particles may sometimes also create a signal of short duration and with a high amplitude, but this will occur to such a little extent that the contribution therefrom can be neglected as compared with the contribution $aPF$; provided the threshold level has been set high enough so that virtually every excursion of the signal above the level in the form of an impulse will represent a scattering from only one or a couple of fibers.

Mostly it is merely interesting to measure the concentration of fibers in excess of a certain size, so-called first-rate fibers, as these fibers represent useful material possible to recover. But many times one is also interested to know the total concentration of suspended substances or, preferably, the concentration of first-rate fibers and the concentration of fine fraction separately. In that case it is possible to use the D.C. level of the obtained signal, as this is also dependent on the concentration of suspended material in the solution. Since big fibers will give high contributions in the form of spikes, but will not give such a great contribution to the D.C. level, this level will substantially represent the turbidity of the liquid. The equation of the size of the D.C. level can be written $Ug = cPF + dFF$, where $c$ and $d$ are constants and FF means the concentration of fibers below a certain size, i.e., the so-called fine fraction. It is easily realized from the discussion that the constant $c$ is considerably less than the constant $d$, but it is by no means negligible. The constants are dependent on the type of fibers and on the angle between the light source and the detector relative to the pipe with the flowing liquid. In order that the method of the invention should function, the signal, whose excursions beyond a definite level are calculated, and the signal, whose D.C. level is indicated, need not be recorded by the same light detector or at the same angle to the incident light. Certainly different constants for different angles are obtained, but the form of the equations is the same, and therefore the angles can be selected so that the most easily read result is obtained in both cases. How the threshold level is arranged and how calculation of the parts in the form of pulses above this level as well as transfer of this calculated result to any form of signal is carried out can be considered as being very well-known technique and need not be reported more in detail. Nor is it necessary to discuss how the formation of the sum $S = PF + FF$ is carried out, when the constants included in the equations are known, as this would be apparent to those skilled in the art and can be carried out in many different ways. Thus the invention consists in combining in a quite definite manner two measuring results obtained according to two different methods.

Of course the method of the invention is not only useful in the wood-processing industry, but can also be utilized in several other connections, where it is desired to find out the concentration of suspended substances in a liquid. This applies in particular to such situations where fractions of different size are present in a liquid, which case is very frequent.

In cases where the liquid may be colored due to substances dissolved in the liquid, a second detecting means should be used in order to obtain the same transmitted light intensity through the liquid. This second means is placed so that radiation penetrating diametrically through the liquid is measured. The result of this measurement is fed to a control means, which adjusts the power to the light source or sources, so that an intensity of light received by the second detecting means is substantially constant.

According to a first embodiment of the inventive device the first detecting means comprises two detectors disposed in different angular positions relative to the direction of the incident radiation, one of said detectors emits the first signal and the other emits the other signal.

According to a second embodiment of the device of the invention the detecting means comprises one single detector, whose output signal is fed to a signal processing means, which develops the two signals from the output signal emitted from this single detector and feeds these on to the evaluation means.

In both the embodiments described above, two light sources may be used which operate with different light wave length and/or illuminate the liquid at different time intervals. The first signal is measured upon illumination with the first light source; and the second signal, upon illumination with the second light source. As an alternative, both the first and the second signal may be measured upon illumination with both the light sources.

BRIEF DESCRIPTION OF THE DRAWING

The invention is described below more in detail with reference to the accompanying drawing, wherein FIG. 1 shows a schematic view of an embodiment of the device of the invention and FIG. 2 shows another embodiment of the device of the invention.

DESCRIPTION OF THE PREFERRED EMBODIMENTS

In FIG. 1 a light source 1 is shown, which illuminates via an optical means 2 a liquid containing suspended substances. The liquid means in a definite position relative to the other stationary means by flowing through a sensing zone such as a pipe 3 which is transparent to the light used. The illumination should take place transversely to the motion direction of the liquid. A detector 4 is arranged at a first angular position $\phi_1$ to the pipe relative to the direction of the incident light, which angle in the embodiment shown is 30° and should preferably be less than 90°, emit a signal in the form of pulses. Each impulse corresponds to a radiation level incident upon detector 4, whose intensity exceeds a predetermined level. The detector 4 is preferably of the type in which radiation incident thereon is determined and converted into an electrical signal and in which a discriminator level is adjustable on the detector means so that only signals in excess of a definite amplitude are fed on to an evaluation means 6. According to experience it is known that the radiation intensity obtained when the incident radiation falls upon and is scattered by particles present in the liquid, is dependent on their size, and therefore each impulse from the detector 4 represents found particles in excess of a predetermined size. The output signal in the form of impulses from the detector 4 is calculated by the evaluation means 6 over a predetermined time interval. The following equation can be set up as a result of this calculation:

$$Uf = aPF + bFF$$

where $Uf$ represents the output signal, PF the concentration of first-rate fibers, i.e., fibers in excess of a definite size, FF the concentration of fine fraction and $a$ and $b$ are constants determined by calibration. As a rule $b$ can be approximately set equal to 0, and in this way the output signal from the detector 4 indicates the concentration of first-rate fibers in the liquid.

A second detector 5 is placed at another angular position $\phi_2$ to the pipe relative to the direction of the incident light, in the case shown is 90°, and which should preferably be in the range 30° to 180°. The detector 5 converts the radiation incident thereon and to an electrical signal. The detector 5 gives as an output signal the D.C. component of the electrical signal produced during the same time as the calculation of the impulses from the detector 4 and this output signal is fed to the evaluation means 6. This signal corresponds to what is generally called the turbidity of the liquid and is represented by the following equation:

$$Ug = cPF + dFF$$

where $Ug$ is the output signal from the detector 5 and $c$ and $d$ are constants, which are determined by means of calibration.

As it is primarily desired to obtain a measure of the total concentration of substances suspended in the liquid the evaluation means 6 will preferably perform the following calculation on the basis of the signals fed thereto from the detectors 4 and 5 (here it is assumed that conditions are such that $b = 0$):

$$PF = Uf/a$$

$$FF = Ug/d - Uf \cdot c/a \cdot d$$

$$S = PF + FF = Uf(\frac{d-c}{a \cdot d}) + Ug/d$$

where S is the output signal from the evaluation means and represents the total concentration of suspended substances in the liquid during the definite time given as the sum of the concentration of first-rate fibers and the concentration of fine fraction. If desired, the evaluation means can also be arranged so that the values of PF and FF are obtained as separate output signals.

In FIG. 1 a second light source 1' is shown with a broken line, the light sources 1 and 1', e.g., operating at different light wave lengths or, alternatively, illuminating the liquid at different time intervals, the light emitted by the one light source and scattered by the substances suspended in the liquid being determined by one of the detectors and the light emitted by the other light source and scattered by the suspended substances in the liquid being determined by the other detector. In the case when the light sources 1 and 1' illuminate the liquid at different time intervals, the output signals of the detectors are determined during the corresponding times, it being assumed in this case that the concentration of fine fraction and the concentration of first-rate fibers during these measurements carried out consecutively are kept relatively constant. Alternatively, several short measuring intervals are selected and average values are formed by the evaluation means. It is also possible to arrange several light sources illuminating the liquid from different angles, which may give a more exact result in certain cases.

In order to obtain the same transmitted light intensity through the liquid in spite of a colored liquid due to substances dissolved therein, a detector 7 is placed so that radiation penetrating diametrically through the liquid is determined. The output signal of the detector 7 is fed to a control means 8 which adjusts the power to the light source or sources so that the intensity of light received by the detector 7 is substantially constant. By this compensation the intensity of the light received from the detectors 4 and 5 is substantially only influenced by the substances suspended in the liquid and not by the substances dissolved in the liquid, and therefore such a compensation should absolutely be carried out in cases where variations in color of the liquid can be expected due to substances dissolved in the liquid. This is often the case in connection with the wood-processing industry.

FIG. 2 shows another embodiment of the device of the invention, where one single detector 9 is used to determine the light spread by the suspended substances in the liquid in another direction than that of the illuminating radiation incident to the liquid. The output signal in the form of an electrical signal is fed to a signal processing device 10, which delivers two component signals to the evaluation means 6. One component signal corresponds to the signal from the detector 4 in FIG. 1; and the other, to the signal from the detector 5 in FIG. 1. In other respects the device according to FIG. 2 corresponds to the device according to FIG. 1. Of course it is possible also in this embodiment to use several light sources. One can for instance use two light sources, which are placed at different angular positions relative to the detector 9, and illuminate the liquid at different time intervals, but during an equally long time, and let the signal processing device deliver the one type of signal at illumination with the one light source and deliver the other type of signal at illumination with the other light source. By this arrangement optimum conditions for finding out the different types of signals can be obtained using only one detector.

As the measurement is carried out substantially continuously at for instance a time interval of some minutes for the measurements, the measuring means can rapidly give alarm if the concentration of suspended substances or one of the components PF or FF should exceed predetermined values. However, the evaluation means can also be carried out so that for instance average day values are reported.

Several different modifications are possible within the scope of invention.

We claim:

1. An analyzing device for determining the concentration of suspended particles in a liquid, said device comprising: means for forming a sensing zone; means for passing a stream of liquid comprising said particles through said sensing zone; means for producing at least one light beam; means for focusing at least one of said light beams into said sensing zone in a direction normal to said stream of liquid, at least one detecting means sensitive to said light beam passing through said stream of liquid, said detecting means being positioned to detect light scattered by said suspended particles in said stream of liquid, for delivering a first output signal having two components, the first one of said components, $Ug$, being a direct current component measured during a predetermined time and corresponding to a detected level of luminous intensity, and the second one of said components, $Uf$, being a pulsed signal measured during the same predetermined time, indicative of the number of times the detected level of luminous intensity has exceeded a predetermined discriminator level, evaluation means for forming a second output signal, S, responsive to said first and second components, said second signal being respresentative of the total concentration of particles suspended in said stream of liquid during the predetermined time; said second output signal being determined by said evaluation means by solution of the equations $Ug = cPF + dFF$ and $Uf = aPF + bFF$, wherein $a, b, c, d$ are constants with $b$ being essentially negligible; PF represents the concentration of suspended particles in excess of a certain definite geometrical size; FF represents the concentration of suspended particles below said size; said second output signal being determined by said evaluation means by solution of the equation $S = PF + FF$.

2. The analyzing device as defined in claim 1, further comprising: second detecting means positioned to detect light transmitted diametrically through said stream of liquid in said sensing zone, the output signal from said second detecting means being supplied to a control means arranged to control the intensity of said at least one light beam, to keep the brightness of the radiation of light received by said second detecting means at a substantially constant value.

3. The analyzing device as claimed in claim 1, wherein said first detecting means comprises two detectors positioned in different angular relationship to the direction of one of said light beams entering said sensing zone, one of said detectors delivering the said first component signal and the other one of said detectors delivering said second component signal.

4. The analyzing device as claimed in claim 1, wherein said first detecting means comprises a single detector, the output signal of which being fed to a signal processing means deriving said two component signals and wherein said component signals are fed into said evaluation means.

5. The analyzing device as claimed in claim 1, wherein said means for producing at least one light beam comprises two sources of light operating with different wave lengths, and wherein said first component signal is derived from the radiation from a first source of light and said second component signal is derived from the radiation from the second source of light.

6. The analyzing device as claimed in claim 1, wherein said means for producing at least one light beam comprises two sources of light operating during different time intervals, and wherein said first component signal is derived from the radiation during a time interval when the first source of light is active and the said second component signal is derived from the radiation during a time interval when the second source of light is active.

7. The analyzing device as claimed in claim 1, further comprising means for indicating at least one of the quantities PF and FF.

* * * * *